United States Patent [19]

Willett et al.

[11] Patent Number: 5,080,098
[45] Date of Patent: Jan. 14, 1992

[54] NON-INVASIVE SENSOR

[75] Inventors: Ronald P. Willett, Bloomington; Dennis K. Dawes; Hammond R. Roudedush, both of Indianapolis; Mark W. Baldwin, Speedway, all of Ind.

[73] Assignee: Sentinel Monitoring, Inc., Indianapolis, Ind.

[21] Appl. No.: 452,700

[22] Filed: Dec. 18, 1989

[51] Int. Cl.$^5$ ............................................. A61B 5/00
[52] U.S. Cl. .................................. 128/633; 128/665; 128/666
[58] Field of Search ....................... 128/633, 665–667, 128/689, 690

[56] References Cited

U.S. PATENT DOCUMENTS

| | | |
|---|---|---|
| 3,359,975 | 12/1967 | Sherman . |
| 3,602,213 | 8/1971 | Howell et al. . |
| 3,698,382 | 10/1972 | Howell . |
| 3,704,708 | 12/1972 | Iberall . |
| 3,810,460 | 5/1974 | Van Nie . |
| 3,815,583 | 6/1974 | Scheidt . |
| 3,847,483 | 11/1974 | Shaw et al. . |
| 3,908,636 | 9/1975 | Page . |
| 3,993,047 | 11/1976 | Peek . |
| 4,013,067 | 3/1977 | Kresse et al. . |
| 4,030,483 | 6/1977 | Stevens . |
| 4,038,976 | 8/1977 | Hardy et al. . |
| 4,086,915 | 5/1978 | Kofsky et al. . |
| 4,091,803 | 5/1978 | Pinder . |
| 4,109,643 | 8/1978 | Bond et al. . |
| 4,129,124 | 12/1978 | Thalmann . |
| 4,183,360 | 1/1980 | Carlson et al. . |
| 4,223,680 | 9/1980 | Jöbsis . |
| 4,259,963 | 4/1981 | Huch . |
| 4,268,751 | 5/1981 | Fritzlen et al. . |
| 4,280,506 | 7/1981 | Zurcher . |
| 4,281,645 | 8/1981 | Jöbsis . |
| 4,301,808 | 11/1981 | Taus . |
| 4,305,401 | 12/1981 | Reissmueller et al. . |
| 4,321,930 | 3/1982 | Jobsis et al. . |
| 4,332,258 | 6/1982 | Arai et al. . |
| 4,334,544 | 6/1982 | Hill et al. . |
| 4,338,950 | 7/1982 | Barlow et al. . |
| 4,347,852 | 9/1982 | Tar . |
| 4,353,152 | 10/1982 | O'Connor et al. . |
| 4,380,240 | 4/1983 | Jöbsis et al. . |
| 4,409,983 | 10/1983 | Albert ................. 128/689 |
| 4,494,550 | 1/1985 | Blazek et al. . |
| 4,510,938 | 4/1985 | Jöbsis et al. . |
| 4,598,700 | 7/1986 | Tamm . |
| 4,685,464 | 8/1987 | Goldberger et al. ....... 128/633 |
| 4,799,491 | 1/1987 | Eckerle ................. 128/640 |
| 4,825,872 | 5/1989 | Tan et al. . |
| 4,830,014 | 5/1989 | Goodman et al. . |
| 4,915,116 | 4/1990 | Hasebe et al. ........... 128/666 |
| 4,938,218 | 7/1990 | Goodman et al. ........ 128/664 |

FOREIGN PATENT DOCUMENTS

| | | | |
|---|---|---|---|
| 0135840 | 4/1985 | European Pat. Off. ...... 128/633 |
| 1128908 | 12/1984 | U.S.S.R. ................ 128/666 |

Primary Examiner—Ruth S. Smith
Attorney, Agent, or Firm—Marjama & Pincelli

[57] ABSTRACT

A sensor for placement against the tissue of a living subject for the purpose of measuring a physiological quantity. The sensor includes a rigid housing having a recess chamber formed therein. A light source and sensor is mounted in a flexible mounting pad secured to the housing. The flexible mounting pad allows the light source and sensor to move independently of each other and conforms to the adjacent tissue.

15 Claims, 4 Drawing Sheets

NON-INVASIVE SENSOR

The present invention relates to an non-invasive sensor for use in determining various physiological measurements of a patient, for example, arterial oxygen saturation heart rate.

BACKGROUND OF THE INVENTION

The non-invasive measuring of certain physiological properties has long been practiced by physicians in the prior art. Such techniques include the transmitting of one or more wavelengths of radiation into perfused tissue and detecting the amount of light passing through or being reflected from the tissue, and using the signal obtained to determine various physiological measurements such as arterial oxygen saturation and heart rate. Examples of prior art devices are illustrated in U.S. Pat. Nos. 4,485,464; 4,086,915; and 3,847,483. The sensors used with such devices are either of the transmissive type, i.e., light being transmitted to a sensor on the opposite side of the tissue, or of the reflective type, wherein the radiation sensed is reflected off the tissue.

A common problem for transmissive and reflectance type sensors is the amount of pressure applied by the sensor against the tissue. It is important the sensor be pressed firmly against the tissue to efficiently use the radiation being transmitted and minimize radiation leakage problems with the sensor. However, too much pressure will cause blood to leave the tissue making it more difficult to obtain accurate measurements. Thus, a delicate balance is needed in order to optimize performance of the sensor. Additionally, patient comfort during prolonged use of the sensor becomes important.

A further problem with transmissive type sensors is that they require the light to pass through the tissue and are thus limited to contain parts of the body such as a digit or an ear. Further, since transmissive type sensors require the radiation detector to be located opposite the radiation source, proper sensor alignment is very critical for optimal operation. Additionally, radiation leakage at the radiation source and sensor can lead to significant measurement errors.

With regard to reflective type sensors, it is also very important that the radiation emitting source be in relatively close proximity to the radiation detector. However, this close proximity presents the risk of radiation leakage from the radiation source to the radiation detector without passing through pulsatile tissue, and therefore provide inaccurate readings. Conformance of the radiation source and detector with the tissue is very important as improper sensor alignment may cause errors in measurement. Further, if insufficient conformance of the detector radiation source exists, the sensor may not operate at all.

Applicants have invented a reflective type sensor which minimizes or avoids the many problems of the prior art.

SUMMARY OF THE INVENTION

A sensor for placement against the tissue of a living subject for the purpose of measuring a physiological quantity. The sensor includes a rigid housing having a recess chamber formed therein. A light source and sensor are mounted in a flexible member pad secured to the housing. The flexible mounting pad allows the light source and sensor to move independently of each other and conforms to the adjacent tissue.

DETAILED DESCRIPTION OF THE INVENTION

Figure 1:
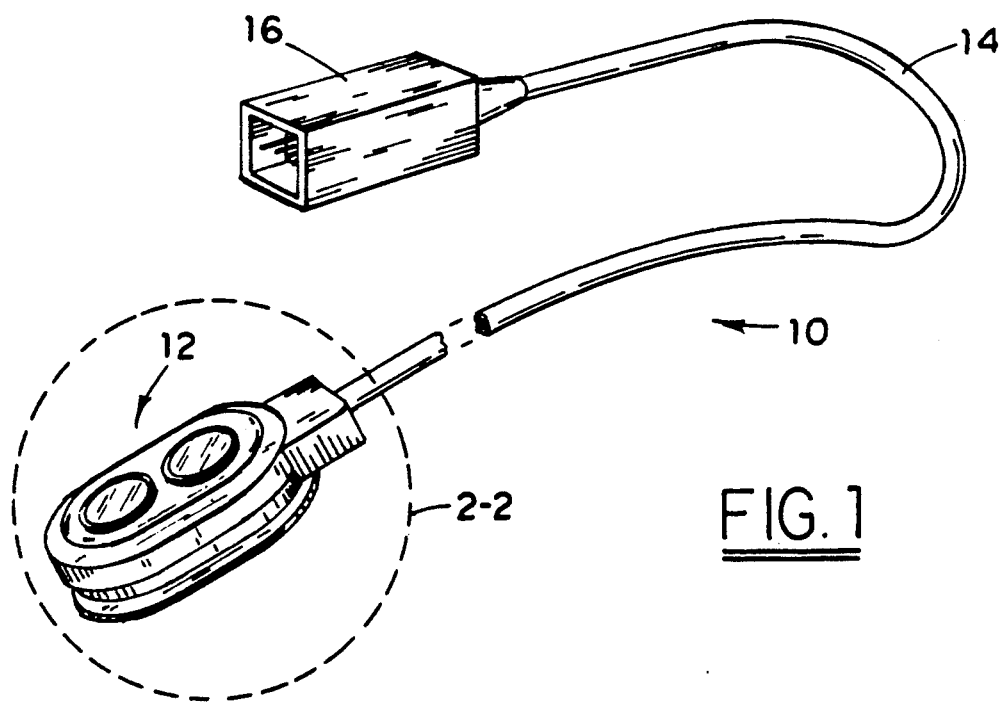
FIG. 1 is a perspective view of a sensor assembly made in accordance with the present invention.
Figure 2:
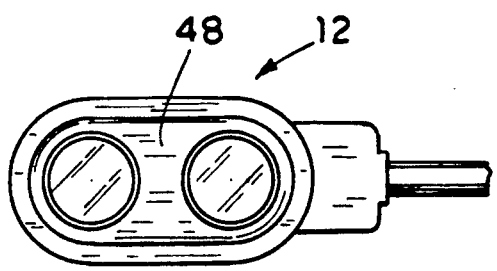
FIG. 2 is a top plan view of the sensor head assembly outlined by line 2—2 of FIG. 1.
Figure 2A:
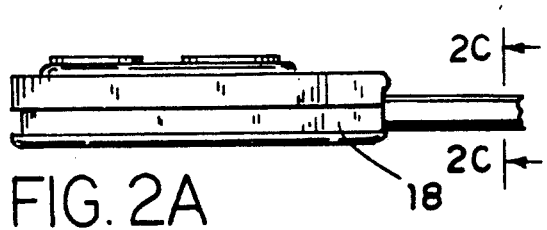
FIG. 2A is a side elevational view of FIG. 2.
Figure 2C:
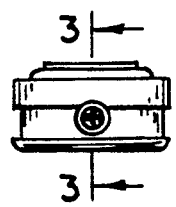
FIG. 2C is an end elevational view of the sensor head assembly of FIG. 2, taken along the line 2C—2C of FIG. 2A.
Figure 2B:
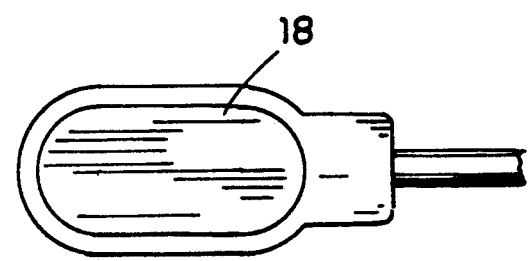
FIG. 2B is a bottom plan view of the sensor head assembly of FIG. 2.
Figure 3:
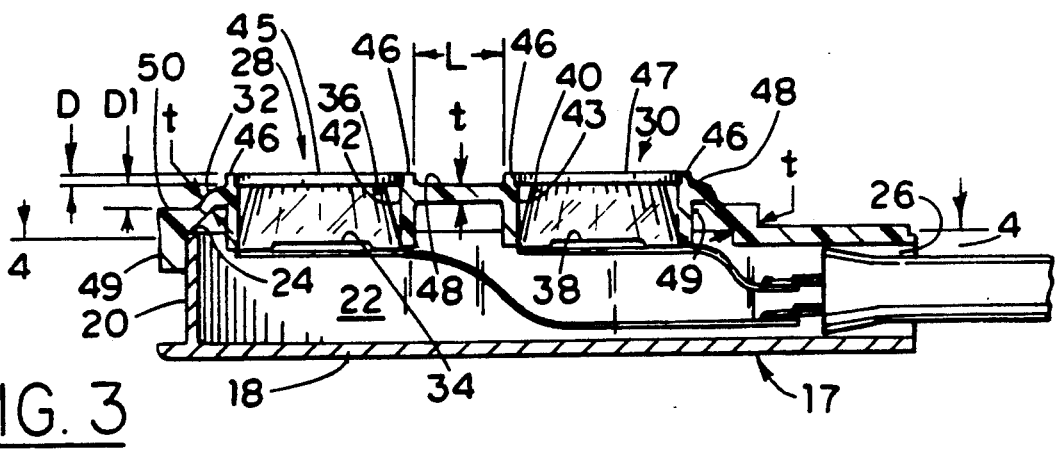
FIG. 3 is an enlarged cross-sectional view taken along line 3—3 of the sensor head assembly of FIG. 2C.
Figure 4:
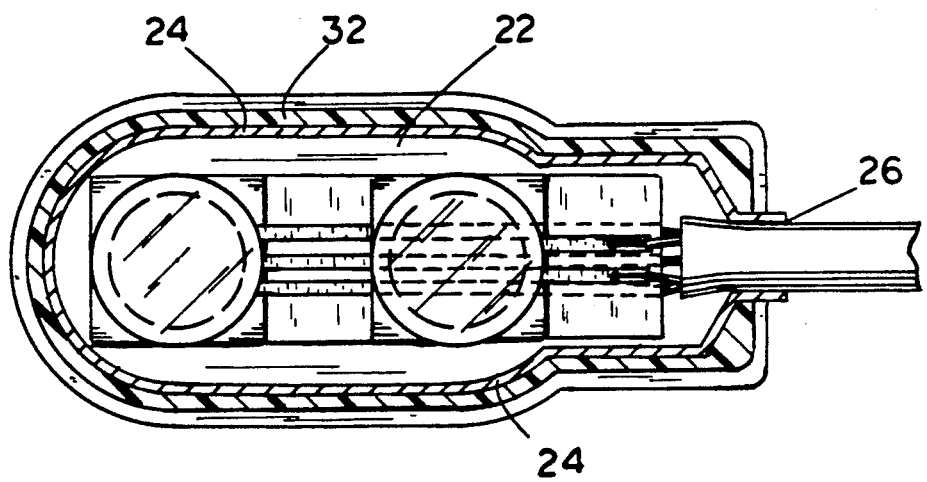
FIG. 4 is an enlarged top cross-sectional view of the sensor head assembly of FIG. 3 taken along line 4—4.
Figure 5:
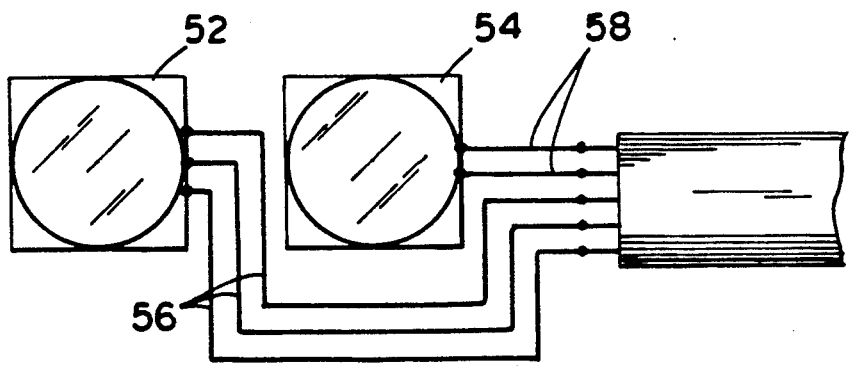
FIG. 5 is an enlarged partial view of the electrical circuitry of the sensor of FIG. 4.

Referring to FIG. 1, there is illustrated a sensor assembly 10 made in accordance with the present invention. The sensor assembly 10 comprises a sensor head assembly 12, a connecting cord 14, and plug 16 at the terminal end of the cord 14 for connecting to an appropriate device for processing the signal received by the sensor head assembly 12. In the particular embodiment, the sensor assembly 10 is designed to be used with a device for measuring arterial oxygen saturation such as described in Applicant's co-pending application Serial No. 07/190,661, filed May 5, 1988, entitled *Pulse Oximetry*, which is hereby incorporated by reference.

Referring to FIGS. 2-7, there is illustrated in more detail the sensor head assembly 12. The sensor head assembly 12 which includes a rigid housing 17 having a rigid base support 18, and a rigid peripheral upstanding wall 20 which extends about the periphery of rigid base support 18 and forms a receiving recess chamber 22. The peripheral upstanding wall 20 terminates at its upper end in an upper rim portion 24. In the particular embodiment illustrated, rigid housing 17 is made out of a hard plastic material, and in particular, of a polypropylene plastic material. Peripheral upstanding wall 20 is provided with an opening 26 to allow cord 14 and with its internal electrical wires to extend within recess chamber 22. The sensor head assembly 12 further include a radiation source 28 and sensing means 30 for detecting reflected radiation from the tissue that emanates from the radiation source 28. In the particular embodiment illustrated, the radiation source 28 comprises two LEDs (light emitting diodes) which produces light at two different wavelengths. In the particular embodiment illustrated, light is produced in the infrared spectrum, and in the red spectrum. Applicants have found that wavelengths of 665 nm (nanometers) and 890 nm (nanometers) work quite satisfactorily for an oximetry sensor. However, it is to be understood that as many or as few radiation sources may be used, and at any desired frequency as may be required for the physiological property being measured. In the particular embodiment illustrated, the sensing means 30 is a photodiode and radiation source 28 is a set of two LEDs, sensing means 30 and radiation source 28 each being placed beneath an individual lens. Appropriate LEDs and photodiodes may be obtained from Optek, Inc. and Shin-Estsu.

The radiation source 28 and the light sensing means 30 are mounted within a flexible support pad 32 which is then mounted to the peripheral upstanding wall 20. Housing 17, pad 32 and cord 14 combine together to form closed chamber. In the particular embodiment illustrated, radiation source means 28 comprises a pair of LEDs 34 mounted in a generally cylindrical hollow clear plastic lens 36 and light sensing means 30 comprises a photodiode 38 also mounted in a generally cylindrical hollow clear plastic lens 40. In the particular embodiment illustrated, the lenses 36 and 40 are of substantially equal size and configuration. In the particular embodiment illustrated, flexible support pad 32 is provided with a pair of openings 42, 32. Each opening 42, 43 being substantially circular in shape and designed to mate and receive the outer surface of the respective lens to be placed therein. Each opening 42, 43 having a diameter of about 0.25 inches (6.35 mm). The lens 36, 40 are secured within opening 42, 43 by the elastic nature of flexible pad 32. However, it is to be understood that lens 36, 40 may be secured to flexible support pad 32 in any desired manner. While substantial identically sized circular openings are preferred, various other sizes and shapes openings may be used as desired. Openings 42, 43 are spaced apart a sufficient distance L to minimize or prevent radiation leakage passing across from the radiation source 28 to the sensor 30, but not too far apart so as to optimize sensing of the reflected radiation. In the particular embodiment illustrated, openings 42, 43 are spaced a distance of about 0.375 inches (9.525 mm). However, is to be understood that any suitable distance may be used keeping the foregoing objectives in mind. Each lens 36 and 40 has an upper contact surface 45, 47 for engagement with the surface of the tissue against which it is to be placed. The support pad 32 is secured to rigid base support 18 by a downwardly extending outer wall integrally formed therewith. The pad 32 may be secured to rigid base support 18 in any desired manner, for example, by being adhesively affixed thereto or by the elastomeric tension of the support pad on the rigid peripheral upstanding wall 20. The support pad 32 is designed such that lenses 36 and 40 can move independently of each other so as to allow the top contact surface 45, 47 of each lens 36, 40 to conform to the surface of the tissue against which it is placed. Additionally, the pad 32 is also designed such that excessive force is not applied to the lenses 36, 40 so as to minimize the loss of blood in the adjacent tissue and provide comfort to the patient. In sensors which rely on the radiation transmissivity of blood, it is important that the tissue against which the sensor is placed not be pressed too hard, as this will cause blood to leave the tissue, thus reducing the sensitivity of the sensor. However, if an insufficient amount of pressure is placed, the risk of light leakage increases which can significantly affect the accuracy of the measurement being taken. It is also very important that the contact surfaces 45, 47 of each lens 36, 40 be oriented in a direction substantially perpendicular toward the tissue. Accordingly, it is important that the contact surfaces 45, 47 conform to the configuration of the adjacent tissue. The support pad 32 is designed such that each lens 36, 40 can independently and freely move within recess chamber 22 and provide a maximum amount of pressure against the tissue. The recess chamber being sized to prevent bottoming of the lenses 36, 40 against rigid base support 18. In the particular embodiment illustrated, the support pad 32 is designed to flex such that a force of about 0.120 lbs. to about 0.130 lbs. is applied against the tissue by the lens 36, 40 when the rim portion 24 is firmly pressed against the tissue in the pad 32. The decreased flexibility of pad 32 may be obtained by the appropriate selection of the material from which pad 32 is made, and providing an appropriate thickness t. Applicants have found that an appropriate elastomeric material from which the support pad 32 may be made is polyvinyl chloride (PVC) with a thickness t of about 0.010 inches. In the particular embodiment illustrated, the polyvinyl chloride has a Shore A hardness of about 55.

The support pad 32 is also designed to minimize radiation leakage from the radiation source 28 to the radiation sensing means 30. This is accomplished by providing pad 32 adjacent each opening 42, 43 with a downwardly extending annular skirt 49 adjacent to the outside surface of the lens 36, 40. Preferably, the pad 32 is made out of a dark non-transparent color, black in this embodiment. Referring back to FIG. 3, immediately adjacent to end openings 42, 43 is a substantially annular ridge 46 integrally formed in the pad 32 so that the contact surfaces 45, 47 is slightly raised above the adjacent top surface 48 of the support pad 32. Applicants have found that the ridge 46 is raised above the top surface 48 a distance D which is generally in the range of about 0.005 inches (0.127 mm). The top surface 48 is raised slightly above the outer rim 50 of the pad which comes into contact with the peripherally upstanding wall 20. Top surface 48 is raised only a slight distance D1 above the periphery 50 so as to provide a further degree of flexibility to the central area of the support pad 32. In the particular embodiment illustrated, top surface 48 extends a distance D1 above the periphery 50.

Figure 6:
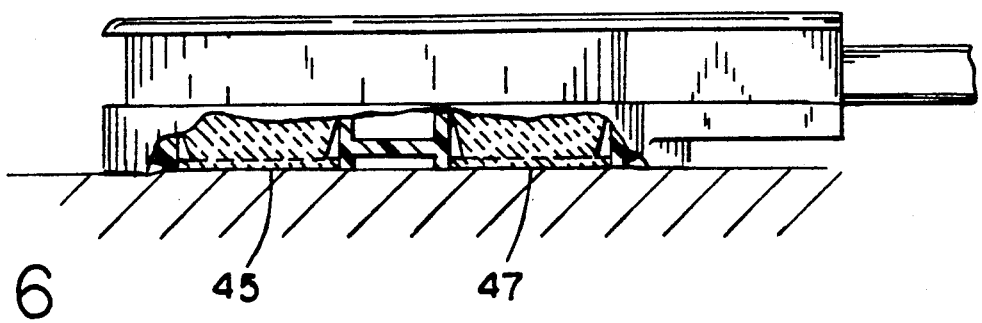
FIG. 6 is an enlarged partial cross-sectional view of the sensor head assembly of FIG. 2 partially broken away as applied against a substantially flat portion of the tissue.
Figure 7:
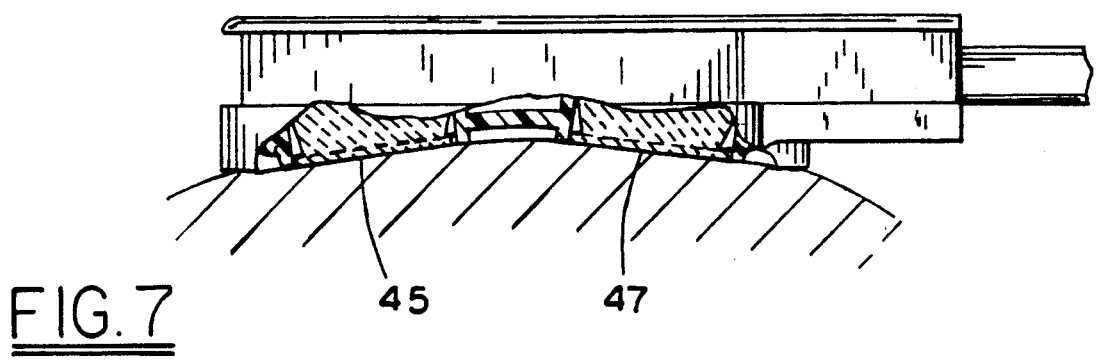
FIG. 7 is an enlarged partial cross-sectional view of the sensor head assembly partially broken away as applied against the finger of a patient.

Referring to FIGS. 6, and 7, there is illustrated a portion of the sensor head assembly 12 as pressed against the forehead and finger, respectively, of an individual. As can be seen, the contact surfaces 45, 47 contacts the surface of the tissue, thus, as radiation is emitted from radiation source 28, radiation sensing means 30 will produce an electrical impulse in response thereto. Flexible electrical circuitry is provided for connecting radiation source 28 and light sensing means 30 for providing appropriate power to radiation source 28 and transmitting a signal from the sensor means 30. In the particular embodiment illustrated, radiation source 28 and light sensing means 30 are appropriately connected by contacts 52, 54, respectively, placed at the back of lens 36, 40 (See FIG. 5) which are appropriately connected to wires 56, 58, which extend into cord 14 which in turn, are appropriately connected to the plug 16 in a manner as is customarily done in the prior art. The contacts 52, 54 and skirts 49 are preferably designed to stop any undesirable radiation from entering or escaping from each lens 36, 40, thus allowing light to leave or enter by the contact surface 44 of each lens. Suitable flexible circuits may be obtained from Nitto-Denko of America.

Figure 8:
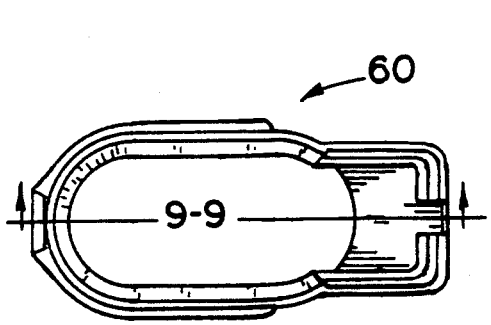
FIG. 8 is a top plan view of an outer flexible housing which is secured to the sensor assembly of FIG. 2.
Figure 10:
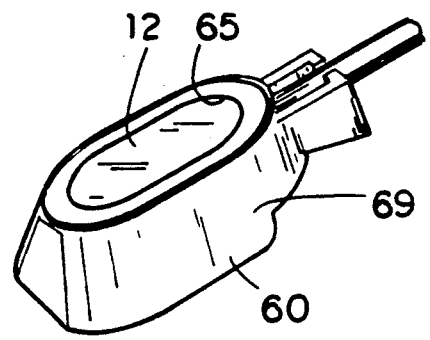
FIG. 10 is a perspective view of the outer flexible housing of FIG. 8 as applied to the sensor head assembly of FIG. 2.
Figure 9:
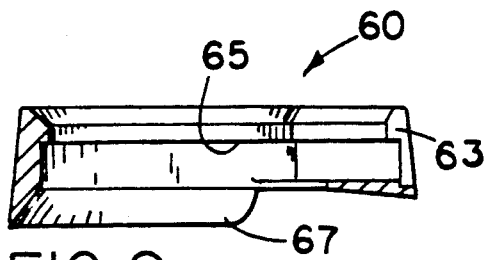
FIG. 9 is a side cross-section view of the outer flexible housing of FIG. 8 taken along line 9—9.
Figure 11:
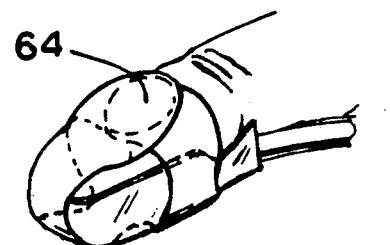
FIG. 11 is a perspective view of sensor head assembly and outer flexible housing of FIG. 10 as applied to the finger of a patient.
Figure 12:
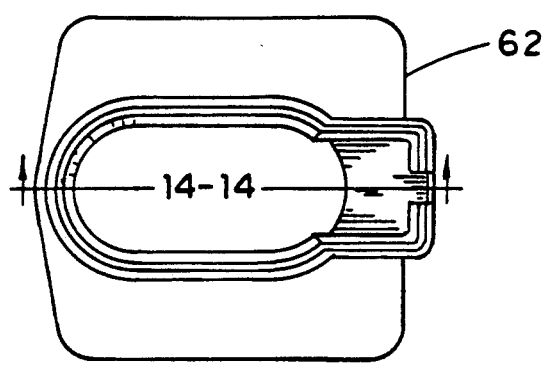
FIG. 12 is a top plan view of a modified outer flexible housing for use with sensor head assembly of FIG. 2.
Figure 13:
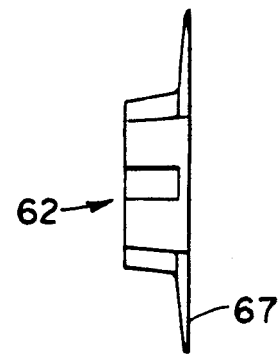
FIG. 13 is an end view of the outer flexible housing of FIG. 12.
Figure 14:
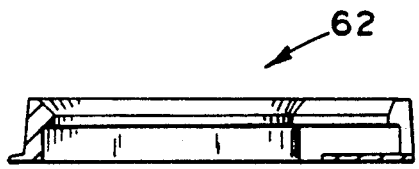
FIG. 14 is a side cross-sectional view of the outer flexible housing of FIG. 12 taken along line 14—14.

Referring to FIGS. 8 through 11 and FIGS. 12-15, there is illustrated outer flexible housings 60 and 62 which are designed to be used with sensor head assembly 12 and placed against tissue of an individual. Outer flexible housings 60, 62 each have an outer peripheral wall 69 which conforms to the outer surface of upstanding wall 20 and pad 32 and forms an opening 65 for receiving sensor head assembly 12. Outer flexible housings 60, 62 are preferably made of an elastomeric material which serves to provide flexibility so as to conform to the shape of the tissue and provide comfort to the patient. Outer flexible housings 60, 62 also provide means for allowing easy adaptation of the sensor head assembly 12 to different parts of the body. However, outer flexible housings 60, 62 are secured to sensor head assembly 12 in any desired manner. The outer flexible housing 60 of FIG. 8 is designed to be used with the fingers and outer flexible housing 62 of FIG. 12 is designed to be placed against the forehead or other alternative anatomical site of an individual. The outer flexible housings 60 and 62, fits around the rigid base 18 and, each having an outwardly extending surface 67 which has a configuration designed to conform to the anatomical site which it is to be placed against and minimizes any potential external light leakage that might reach radiation sensing means 30. Outer flexible housings 60, 62 also provide means whereby the sensor head assembly can be easily secured to the patient. In particular, outer flexible housings 60, 62 provides means for allowing a strip of adhesive tape to secure the sensor head assembly 12 against the tissue. FIG. 9 is a cross sectional view of sensor 60 illustrating opening 63 in which the wire cord is received. FIG. 10 illustrates the sensor head assembly 12 with the outer flexible housing 60 assembled thereto. Referring to FIG. 11, there is illustrated the light sensor assembly 12 and outer flexible housing 60 as placed against the finger of a patient and secured by an adhesive tape 64 having a generally T-shaped configuration. As can be seen, the adhesive tape 64 is simply secured to the back of the rigid base support 18 and the 12 is provided for use with a single one of the outer flexible housings 60, 62. However, if desired, outer flexible housings 60, 62 may be provided for interchangeably with a single head assembly 12. FIGS. 13 and 14 illustrate an end view and cross sectional view, respectively, of housing 62.

Figure 15:
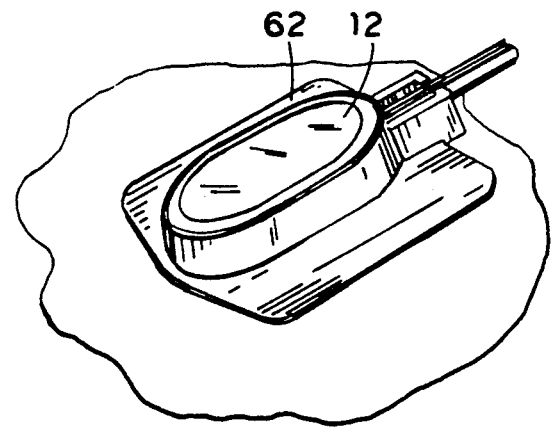
FIG. 15 is a perspective view of the sensor head assembly and outer flexible housing of FIG. 12 adjacent the forehead of a patient.
Figure 16:
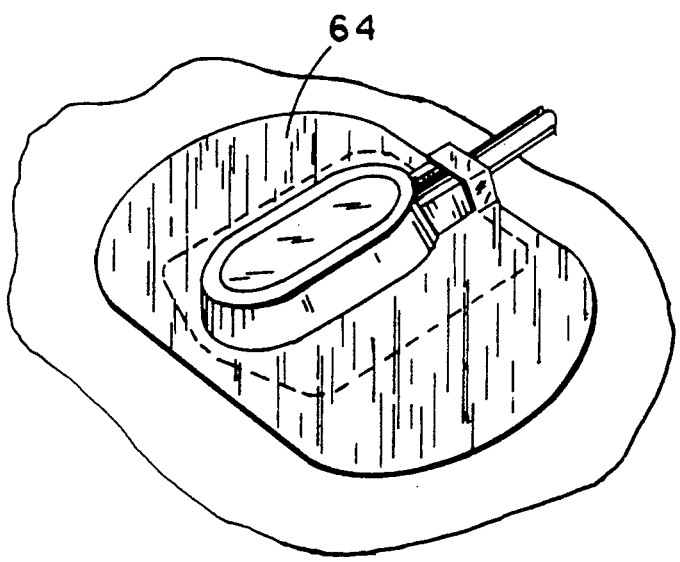
FIG. 16 is a view of the sensor head assembly of FIG. 15 secured to the patient by an appropriate tape.

Referring to FIG. 15, there is illustrated a single sensor head assembly 12 having the outer flexible housing 62 adjacent the forehead of a patient, and FIG. 16 illustrates the sensor head assembly of FIG. 15 secured to the forehead of an individual by an adhesive tape 66.

In the particular embodiment illustrated, adhesive tape 66 has a configuration designed to receive therethrough a portion of the head assembly, It is of course, understood that the configuration of tape 64, 66 may take any desired configuration.

In order to more fully understand the operation and use of the sensor, applicants will describe in detail the placement and use of the sensor. First, the operator selects the appropriate sensor head assembly 12 to be used having the desired flexible outer housing. For example, if the sensor is to be placed against the finger, the sensor head assembly 12 having outer flexible housing 60 as illustrated in FIG. 8 would be selected, or if the sensor is to be placed against a substantially flat portion of the body, such as the forehead the sensor head assembly 12 having outer flexible housing 62 would be selected. The sensor head assembly 12 is placed against the appropriate portion of the body, at which time the contact surface 45, 47 of each of the lenses 36, 40 initially contact the tissue. The sensor head assembly 10 is pressed against the individual and is limited in its movement by the peripheral upstanding wall 20 of rigid base 18. As the rigid base 18 is pressed against the tissue, the lenses are free to independently move and redirect its contact surface 45, 47 so as to properly conform to the adjacent tissue and deflect within the pad 32 a sufficient amount so that the appropriate amount of force is exerted against the tissue. Each lens 36, 40 accomplishes this independently of the other. Thereafter, the sensor head assembly 12 is simply secured by an appropriate strip of adhesive tape as illustrated in FIGS. 11 and 15. Thereafter, the apparatus used with sensor assembly 10 is operated, as is well known and described in the prior art. For example, as described in applicants co-pending application previously discussed. After obtaining the appropriate measurements, the sensor is simply removed by removing the strip of adhesive tape used to secure the sensor to the patient.

It is to be understood that various other changes and modifications can be made without departing from the spirit and scope of the present invention.

We claim:

1. A sensor for placement against the tissue of a living subject for the purpose of measuring a physiological quantity, said sensor comprising:
   a rigid housing having a rigid peripheral upstanding wall which forms a recess chamber, said upstanding peripheral wall terminating in an upper rim designed for providing a force against the tissue of a patient and limiting the amount of movement of said housing;
   light source means for exposing said tissue to a source of light having at least one predetermined wavelength;
   light sensing means for sensing light reflected from said tissue which has been exposed to said light source means;
   flexible support means secured to said housing and placed against said upper rim for independently supporting said light source means and light sensing means within said recess chamber and for placement against the tissue of a patient, said light source means and light sensing means being mounted in said flexible support means such that said light sensing means and light source means move independently from each other and conform to the tissue of the patient.

2. A sensor according to claim 1 wherein said flexible support means comprises a flexible support pad made of an elastomeric material, said support pad having a pair of openings therethrough, one of said openings receiving and holding said light source means and the other opening receiving and holding said light sensing means.

3. A sensor according to claim 2 wherein said pad is made of polyvinyl chloride.

4. A sensor according to claim 1 further comprising an outer housing for placement adjacent the outer periphery of said upstanding wall.

5. A sensor according to claim 4 wherein said outer housing has a configuration shaped so as to conform to the tissue against which the sensor is placed.

6. A sensor according to claim 1 further comprising flexible electrical circuitry means for providing appropriate power to said light source means and for transmitting a signal from said light sensing means.

7. A sensor according to claim 1 wherein said flexible support means is secured to the top of said upper rim.

8. A sensor according to claim 1 wherein said light source means and light source sensing means each have a lens for contacting the tissue of the patient.

9. A sensor according to claim 1 wherein said light sensor means and light sensing means are spaced apart a distance of about 0.375 inches.

10. A sensor according to claim 1 wherein said flexible support means is designed such that when said sensor is placed against the tissue of the living subject, the force exerted on the tissue by said light source means and light sensing means is in the range of about 0.120 lbs to 0.130 lbs.

11. A sensor according to claim 1 further comprising an outer flexible housing secured to said rigid housing for adaption of said sensor to tissue of said patient.

12. A sensor according to claim 1 wherein said light source means and light sensing means are designed so that said physiological quantity being monitored is arterial blood oxygen saturation.

13. A sensor according to claim 12 wherein said light source means includes a first light source which emits light at 890 nm and a second light source which emits light at 665 nm.

14. A sensor according to claim 12 wherein said light sensing means comprises a photodiode.

15. A sensor according to claim 1 wherein said light source means and said light sensing means are designed so that said physiological quantity being monitored is heart rate.

* * * * *